United States Patent [19]

Sitte et al.

[11] Patent Number: 5,686,313
[45] Date of Patent: Nov. 11, 1997

[54] METHOD FOR PREPARATION OF MICROSCOPIC, ESPECIALLY ELECTRON-MICROSCOPIC, SLIDES FOR THE PREPARATION OF SECTIONS

[75] Inventors: Hellmuth Sitte, Seefeld in Tirol, Austria; Ludwig Edelmann, Homburg-Saar, Germany

[73] Assignee: Leica AG, Vienna, Austria

[21] Appl. No.: 232,080

[22] PCT Filed: Aug. 26, 1993

[86] PCT No.: PCT/EP93/02296

§ 371 Date: Jun. 1, 1994

§ 102(e) Date: Jun. 1, 1994

[87] PCT Pub. No.: WO94/05994

PCT Pub. Date: Mar. 17, 1994

[30] Foreign Application Priority Data

Sep. 8, 1992 [AT] Austria ................... 1786/92

[51] Int. Cl.⁶ .................................................. G01N 1/36
[52] U.S. Cl. ............................ 436/176; 118/423; 118/500; 422/100; 422/101; 422/102; 422/104; 427/2.11; 436/174; 436/178
[58] Field of Search .......................... 436/174–178, 436/180; 422/63, 99–102, 104; 427/4, 508, 512, 2.11, 2.13; 118/423, 428, 429, 500, 620, 50.1

[56] References Cited

U.S. PATENT DOCUMENTS

| | | | |
|---|---|---|---|
| 2,341,197 | 2/1944 | Weiskopf | 118/429 |
| 2,783,180 | 2/1957 | Whitehead | 118/423 |
| 3,338,207 | 8/1967 | Kling | 118/429 |
| 3,809,008 | 5/1974 | Takahashi | 118/429 |
| 4,196,231 | 4/1980 | Hubers | 118/423 |
| 4,202,289 | 5/1980 | Bils | 118/423 |
| 4,306,425 | 12/1981 | Sitte et al. | 62/51.1 |
| 4,363,783 | 12/1982 | Sitte | 422/68 |
| 4,723,420 | 2/1988 | Sitte | 62/51.1 |
| 4,839,194 | 6/1989 | Malluche et al. | 427/2 |

FOREIGN PATENT DOCUMENTS

| | | |
|---|---|---|
| 0 136 014 | 4/1985 | European Pat. Off. . |
| 29 44 464 | 5/1981 | Germany . |
| 30 42 578 | 6/1982 | Germany . |
| 34 25 744 | 1/1986 | Germany . |

OTHER PUBLICATIONS

H. Sitte, Mts–Extra Nr. 10, Umschau–Verlag Breidenstein GmbH, Frankfurt–Main, 1985.

H. Sitte et al., published in G. Schimmel und W. Vogell, "Methodensammlung der Elektronenmikroskopie", *Methods of Electron Microscopy With English Summaries*, Wissenschaftliche Verlags–GmbH, Stuttgart, Lieferung 11, (1983), insbesondere pp. 184–191 and Figs. 100a und 101.

B. Hurnbel et al., published in M. Mueller et al., "Freeze Substitution And Low Temperature Embedding", *The Science Of Biologies Specimen Preparation*, SEM Inc., Chicago, pp. 175–183, (1986).

(List continued on next page.)

*Primary Examiner*—Jan Ludlow
*Attorney, Agent, or Firm*—Foley & Lardner

[57] ABSTRACT

Method for the incubation of specimens (7) in fluids (5) for subsequent embedding in capsules by polymerization, the specimens (7) being put into hole capsules (2') which are open at the top and, in the lower third of their cylindrical wall, have at least a circle of passage orifices (6) which are smaller than the diameter of the specimens (7). These specimens (7) are incubated in a fluid (5) extending above these passage orifices (6). The hole capsules (2') are then introduced into enveloping capsules (3) of a larger diameter and with a likewise preferably cylindrical wall, a fluid (5) (a polymerizable monomer batch) present in the enveloping capsules (3) filling at least the gap (S) between the hole capsule (2') and the enveloping capsule (3), and this fluid (5) being finally polymerized under UV radiation or action of heat. The hole capsules (2') and the enveloping capsules (3) can be successively slipped over rams (4') which are located on a carrier (1).

18 Claims, 2 Drawing Sheets

OTHER PUBLICATIONS

E. Carlemalm et al., "Resin Development For Electron Microscopy And An Analysis Of Embedding At Low Temperature", *Journal of Microscopy*, Oxford vol. 126: 123-143, (1982).

H. Sitte et al., published in A. J. Verkleij und J. L. M. Leunissen, "Immuno-Gold Labeling In Cell Biology", pp. 64-93, Chapter III, Rapid Freezing, Freeze-Substitution And Resin Embedding, CRC-Press, Boca Raton, Florida, USA (1989).

H. Sitte, Zeiss Information, MEM 3, "Magazine For Electron Microscopists", pp. 25-31, (1984).

H. Sitte, et al., "An Instrument for Cryosubstitution and Low Temperature Embedding", GIT Labor-Medizin, No. 5, 1987, pp. 199-208.

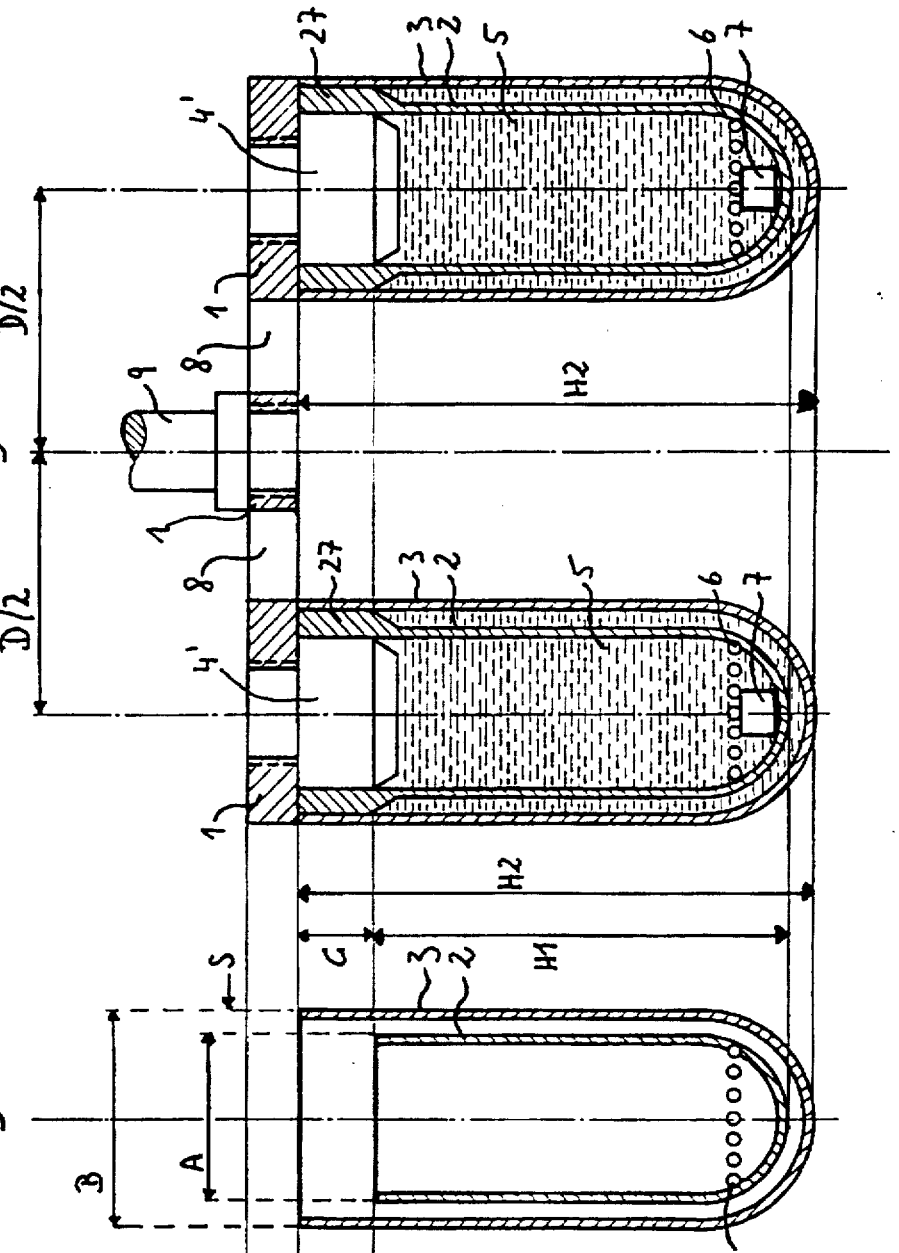

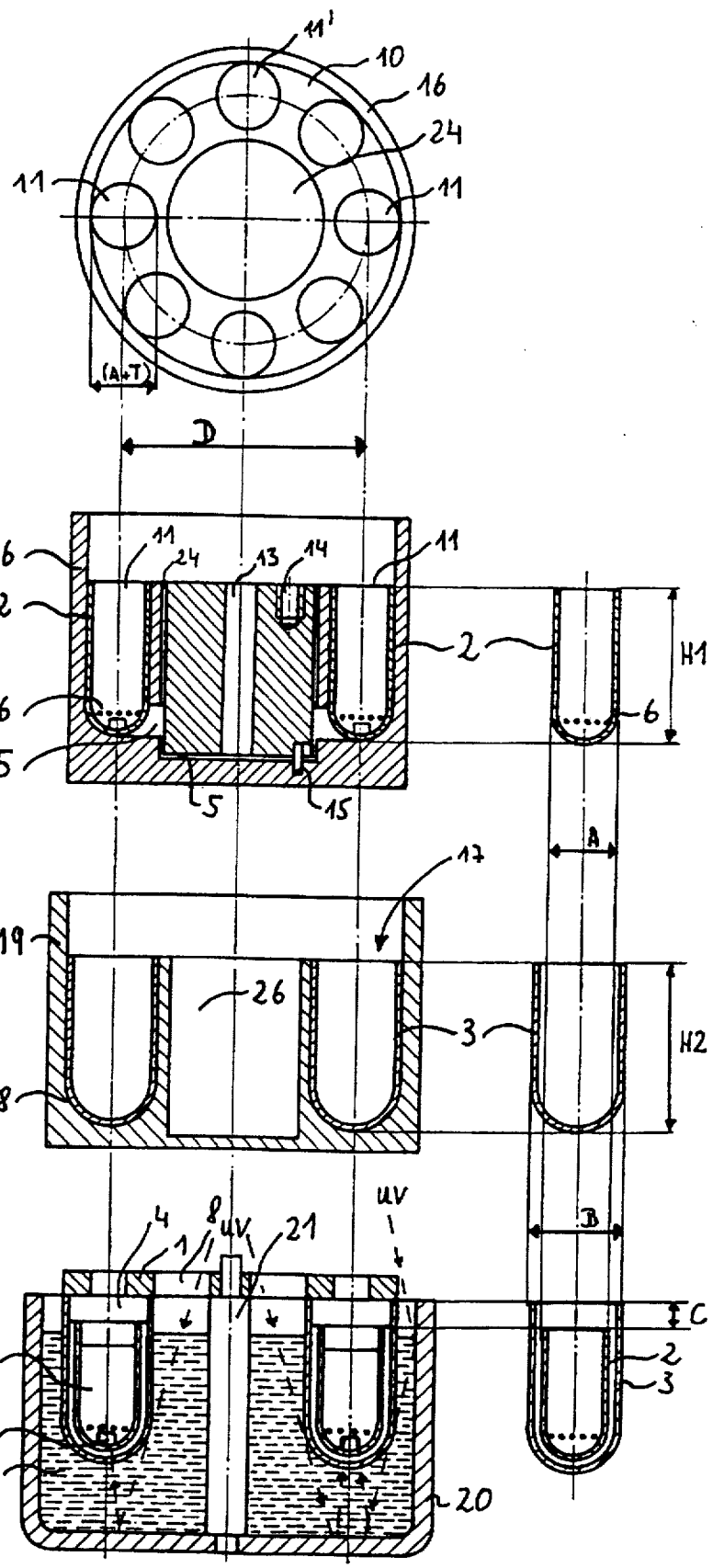

METHOD FOR PREPARATION OF MICROSCOPIC, ESPECIALLY ELECTRON-MICROSCOPIC, SLIDES FOR THE PREPARATION OF SECTIONS

BACKGROUND OF THE INVENTION

1. Field of the Invention

The invention relates to a method for the incubation of specimens in fluids, especially for subsequent embedding in capsules by polymerization. The embedding by polymerization, which is preferably carried out at temperatures between −120° C. and +80° C., serves for preparing the specimens for a subsequent preparation of sections for microscopic, especially electron-microscopic, end histochemical investigations.

2. Description of the Related Art

As an alternative to the now current standard methods (chemical fixation in buffered solutions of aldehyde and/or osmiumtetroxide—dehydration in polar organic media—incubation in monomer—embedding in synthetic resin by polymerization; cf. H. Sitte, mta-Extra No. 10, Umschau-Verlag Breidenstein GmbH, Frankfurt-Main, 1985), biological specimens are to an increasing extent frozen in extremely rapidly ("cryofixation"). Subsequently, the ice contained in the specimens is dissolved out at temperatures between about −80° C. and −120° C. by incubation of the frozen specimens in polar organic fluids (for example methanol or acetone) and replaced by these media ("Cryosubstitution: in this connection, cf. inter alia Patent Specifications DE 2,944,464 C2 or DE 3,425,744 C2, or H. Sitte, Zeiss, MEM 3, 25–31, 1984, or H. Sitte et al., GIT Labor-Medizin 10, 199–208, 1987, or H. Sitte et al. in A. J. Verkleij and J. L. M. Leunissen as editors of "Immuno-Gold Labeling in Cell Biology, pages 64–93, and in particular chapter III "Rapid Freezing, Freeze-Substitution and Resin Embedding", CRC-Press, Boca Raton, Fla., USA, 1989; more extensive literature references are included in the latter) and, finally, an embedding by polymerization, initiated by UV irradition, is carried out at low temperature after incubation in a monomer. The alternative "PLT method" (PLT represents "Progressive Lowering of Temperature; in this connection, cf. also embedding at low temperature, inter alia, E. Carlemalm et al., J. Microscopy, Oxford 126, 123–143, 1982, and B. Hurnbel and M. Müller in M. Müller et al., editors of "The Science of Biological Specimen Preparation", SEM Inc., Chicago, pages 175–183, 1986; further literature references are included in the latter) starts from a weak chemical fixation of the specimens (for example in buffered aldehyde) and lowers the temperature of the specimens continuously at steadily increasing concentration of the added polar media (for example methanol) to that extent which corresponds to the freezing point of the particular mixture. This method also concludes with a low-temperature embedding by UV. According to the state of the art, this embedding is as a rule carried out by stepwise transfer of the largely dehydrated specimens into a monomer batch, followed by polymerization by means of UV irradition at temperatures between −30° C. and −70° C.

Both the preparation steps according to the standard method and the said methods at reduced temperature involve a multiple change of the dehydration or substitution media and a stepwise transfer into the pure monomer batch, which has to be carried out individually for each preparation in the case of using Eppendorf tubes for work at reduced temperatures and is extremely time-intensive in the case of relatively large quantities of specimen. A particularly adverse factor is that all individual containers must be sealed gas-tight individually before the UV polymerization at reduced temperature, since otherwise individual components vaporize and perfect curing of the synthetic resin is no longer possible. Further problems are caused by the fact that numerous fixation solutions and substitution media contain powerful poisons having a high vapor pressure (for example the volatile $OsO_4$) and the usual monomer batches contain powerful allergens, so that both inhalation of the vapors and skin contact can trigger serious illnesses.

SUMMARY OF THE INVENTION

It is the object of the present invention to simplify the embedding in capsules by the standard method, especially also in the case of reduced temperature, and thus both to save time and to minimize the risk of skin contact with allergens and inhalation of volatile toxic substances. This applies in particular to the synchronous preparation of a plurality of different specimens. One solution is achieved according to the invention in such a way that the specimens are first put into capsules ("hole capsules") which are open at the top and, in the lower third of their preferably cylindrical wall, have at least one passage orifice which is smaller than the diameter of the specimens, that at least one fluid is filled in via this or these passage orifice(s) and the specimens are in each case incubated therein, and that the hole capsules are subsequently introduced into capsules of larger diameter ("enveloping capsules") likewise having a preferably cylindrical wall, a fluid present in the enveloping capsules filling at least the gap between the hole capsule and the enveloping capsule.

The orifice or orifices in the hole capsules (preferably these represent a circle of orifices) thus each have a diameter which permits the ingress and egress of fluids but, due to its dimension, precludes egress and hence a loss of objects. In the simplest case, these hole capsules are introduced by means of tweezers successively into the various media which are in bottles or small containers. During the immersion from below through the orifice(s) they are thus filled with the medium which flows off again after lifting. In the last step, the hole capsule is filled with a monomer batch, e.g., an organic fluid, capable of polymerization. In order to prevent this monomer from flowing out, the hole capsule is later introduced into an "enveloping capsule" which is at least partially filled with monomer and whose internal diameter is only slightly greater than the external diameter of the hole capsule. The monomer then fills the gap between the hole capsule and the enveloping capsule and can subsequently be polymerized in the known manner by heat or UV irradition, capsules of UV-permeable materials, especially polyethylene, polypropylene, acetal resin or gelatine, being envisaged for the UV-polymerization.

In addition to the method according to the invention, the invention also relates to special apparatus, in particular for carrying out the method according to the invention, namely the hole capsules which are to receive a specimen, the enveloping capsules which are to receive the hole capsule which can be filled with a specimen, a holder and a mounting device for holding at least one hole capsule and/or at least one enveloping capsule, and a fluid-bath container with a mounting for the holder of the hole capsule and/or enveloping capsules and, finally, especially for carrying out the method according to the invention, a system for incubating specimens in fluids, having at least two and preferably all of the following components:

at least one hole capsule, at least one enveloping capsule, a mounting device for at least one hole capsule, a mounting device for at least one enveloping capsule, a holder for handling at least one hole capsule and at least one enveloping capsule, and a fluid-bath container.

In fact, a commercially available tool (for example tweezers, as already mentioned) can be used for carrying out the method according to the invention. It is advantageous, however, to use a special mounting component for holding the specimens, for example a ram provided with a central bore, and a holder for this ram, for example a sleeve-shaped carrier. For example, it is possible in this way without any risk to fill a number of small test tubes with the various media, to place the specimen in the hole capsule each time for a defined period into such a vessel and then to lift the system consisting of a holder, the ram and the specimen present in the hole capsule and to transfer it into the next medium, after the first medium has run out. An advantageous embodiment of the apparatus for carrying out the method can provide that, on a carrier, a plurality of hole capsules are present on a plurality of rams, so that a virtually unlimited number of specimens and hole capsules can be synchronously transferred from one medium into the next.

A further embodiment of the apparatus for carrying out the method according to the invention can provide that there are at least two hole capsules in a container in a defined geometric arrangement. After the dehydration medium or substitution medium has been filled into a central orifice of the container, all the hole capsules present in the container are filled in a single working step by introducing a substitution body through the perforations of the hole capsules. Convection of this medium is accomplished in a simple manner synchronously for all specimens by lifting and repeated lowering of this substitution body. Media changes are likewise carried out synchronously for all preparations by extracting the old medium through a channel which is provided in the substitution body and through which the new medium is also filled in. After the incubation with monomer has been concluded, the hole capsules filled with monomer are, again in one working step, placed in the manner already described onto rams which are located on a carrier in the same geometrical arrangement as that of the hole capsules in the container described. The perforations of the hole capsules are then in turn closed in a single working step by inserting them into the already mentioned enveloping capsules which have a slightly larger diameter and which are likewise filled beforehand at least partially with monomer batch, these enveloping capsules being arranged in a further container in the same geometrical manner as the rams on the carrier or the hole capsules in the container described above. The monomer-filled enveloping capsules are, for example, placed onto a second step of a stepped ram and adhere to this step in the same way as the hole capsules adhere to a lower step of the stepped ram in strict sliding fit. In view of the subsequent preparation of sections (in this connection cf. H. Sitte, 1985, l.c.), the distance between the outer surface of the hole capsules and the inner surface of the enveloping capsules is about 0.5 to at most 2 mm. After the enveloping capsules have been put on, all the capsules are transferred together with the carrier by means of a manipulator for thermal polymerization into a thermostat, or, for low-temperature embedding, into a pot which is filled approximately to the lower rim of the ram with fluid (for example alcohol) which accelerates removal of the heat arising during the exothermic polymerization reaction. For operation in the cold room, the manipulator mentioned a number of times is fitted with a heat-insulating handle.

A further advantageous embodiment of the method according to the invention and of the types of apparatus designed for carrying out this sequence of the method can comprise at least a part of these operations being carried out by an automatic device without intervention of the user.

Thus, for example, the hole capsules in the described container can be filled manually, but the hole capsules with the slides are then introduced into a "tissue processor" (automatic embedding machine) which, for example in the manner of a "rotary system or drum system" (in this connection, cf. H. Sitte and K. Neumann in G. Schimmel and W. Vogell, editors of "Methodensammlung der Elektronenmikroskopie [Collection of Electron-Microscopic Methods]", Wissenschaftliche Verlags-GmbH, Stuttgart, issue 11, 1983, in particular pages 184–191 and FIGS. 100a and 101), lowers each of the capsules successively into a container with a medium, generates convection, which degrades gradients which may have built up, by repeated lifting and lowering as required, then lifts them and, after the first medium has dripped off, transfers the hole capsules with the specimens on the carrier into the next vessel filled with another medium. After completion of the monomer impregnation, all the hole capsules can be inserted together automatically or manually in the manner already described into the enveloping capsules and passed to polymerization. In contrast to all systems hitherto known from the state of the art, this operation can be carried out without particular training with minimum time spent and without the risk of skin contact with allergens or of inhalation of toxic gases.

BRIEF DESCRIPTION OF THE DRAWINGS

The method according to the invention and the types of apparatus serving to carry it out are explained in more detail below by embodiment examples with reference to the rough diagrammatic drawings, in which:

FIG. 1a shows an individual hole capsule with a slide on a stepped ram which is located on a manipulator with a handle, the hole capsule being immersed in a medium and being filled with the latter, which is in a container, in a diagrammatic cross-section, FIG. 1b shows a hole capsule and an enveloping capsule for the system according to FIG. 1a in a diagrammatic cross-section with dimensional data for the diameter and wall thickness of the capsule and of the gap space formed between the two capsules during the placing onto the stepped ram according to FIG. 1a, FIG. 1c shows two hole capsules with a beaded edge on simple rams on a perforated carrier located on a manipulator, the enveloping capsules being slipped over the beaded edge of the hole capsules, and the hole capsules being charged with slides and both capsules being filled with monomer batch, in a diagrammatic cross-section, and FIG. 2a shows a container with two orifices for taking up hole capsules, in diagrammatic plan view (further orifices indicated in broken lines), FIG. 2b shows the container according to FIG. 2a with inserted hole capsules and an inserted substitution body, in a diagrammatic cross-section, FIG. 2c shows a container for mounting enveloping capsules with inserted enveloping capsules, in a diagrammatic cross-section, and finally FIG. 2d shows a perforated carrier with two charged twin capsules on a stand in a fluid-filled pot for UV polymerization, the twin capsules containing the slides and the monomer batch.

All the individual illustrations in FIG. 2 correspond with respect to the dimensions, in particular with respect to the distance D between the orifices for the hole capsules and enveloping capsules in the containers, and the rams on the carrier which serve to take up the hole capsules and enveloping capsules.

DETAILED DESCRIPTION OF THE PREFERRED EMBODIMENTS

FIG. 1a shows a simple embodiment of an apparatus for carrying out the method according to the invention, a preferably cylindrical hole capsule 2 with an external diameter A and a wall thickness W being slipped in strict sliding fit over the lower step of a stepped ram 4 with a diameter (A–2 W) and the stepped ram 4 having a second step with a diameter (B–2 W), later serving for slipping on an enveloping capsule 3. For aeration and venting, the stepped ram 4 has a central bore 28 and is fixed to a simple manipulator 9' (for example a sleeve) with a handle 29. In its lower third, the hole capsule 2 has at least one orifice, a circle of orifices 6 in the case shown, whose diameter is significantly smaller than the diameter of the specimen 7. The system 2,4,7,9',29 can be immersed into a container 30 and into the medium 31 (for example an aldehyde solution for chemical fixing of the specimen 7) present therein, the capsule 2 being filled from below through the orifices 6 with the medium 31, and the air initially present in the capsule 2 escaping through the orifice 28 in the stepped ram 4 and subsequently through the manipulator sleeve 9'. The method according to the invention can be accelerated by a vertical up-and-down movement of the system 2,4,7,9',29 in the direction of the double arrow, concentration gradients on the surface of the specimen 7 being degraded by the convection of the fluid 31 leaving or entering through the row of holes 6. For the polymerization, an enveloping capsule 3 at least partially filled with monomer batch 5 is slipped in the manner indicated in broken lines over the second step of the ram 4, and the system 2,3,4,5,7,9',39 is transferred into a thermostat for thermal polymerization or into a low-temperature system for UV polymerization (in this connection, cf. FIG. 2d). As a result of handling by means of the manipulator 9',29, after the object 7 has initially been introduced into the hole capsule 2 and the latter has been slipped over the stepped ram 4, any risk of skin contact with an allergen and, during work under the fume hood, any risk of an inhalation of toxic gases are avoided in a very simple manner.

FIG. 1b shows the dimensions and the relative respective positions of the hole capsule 2 and enveloping capsule 3 used according to FIG. 1a. For example, the hole capsule has an external diameter A and a wall thickness W and a height H1, and the enveloping capsule 3 has an external diameter B and a wall thickness W and a height H2. The strict sliding fit on the stepped ram 4 extends in each case up to a height section C. The gap between the outer surface of the hole capsule 2 and the inner surface of the enveloping capsule 3 corresponds to S. The row of holes 6 is preferably located approximately in the half of the hemispherical lower section of the hole capsule 2, the individual holes having a diameter D.

The external diameters A and B of the capsules 2 and 3 are of the order of magnitude, useful for block embeddings, of between about 4 and 10 mm, their wall thicknesses are of an order of magnitude of between 0.1 and 0.5 mm and their heights H1 and H2 are of an order of magnitude of between about 8 and 15 mm. The height C of the steps on the stepped ram 4, fixed to the carrier 9' for example, are in each case about 2 to 4 mm. The gap S between the outer surface of the hole capsule 2 and the inner surface of the enveloping capsule 3 amounts to about 0.5 to 2 mm, and the diameter of the holes is about 0.2 to 1 mm.

In contrast to FIG. 1a, the design according to FIG. 1c allows the method, within the scope of the invention, to be carried out with in each case at least two twin capsules 2', 3 in one working step in each case. As distinct from FIGS. 1a and b, the hole capsules 2' are in this case located on simple rams 4' without steps, which are fixed to a carrier 1, for example screwed to the latter, which has orifices 8 to allow the passage of UV irradition (cf. FIG. 2d). The hole capsules 2' sit on the ram 4' in strict sliding fit under the conditions explained in FIG. 1a and, in the region C themselves have a beaded edge 27 to which the enveloping capsules 3 can be applied likewise in strict sliding fit. According to the illustration in FIG. 1c, the capsules 2', 3 including the gap S are filled with monomer batch 5 and are thus ready for polymerization of the monomer 5. For this purpose, the carrier 1 can be transferred by means of a manipulator 9 which can be joined to the carrier 1, for example by screwing.

For carrying out the individual steps of the method according to the invention, and for the design of the further constituents of the system according to the invention of types of apparatus, the geometrical positional relationships of the various components, and according to FIGS. 1 and 2, especially the distance D between the parallel axes of the two rams 4 and 4', illustrated by way of example, play a decisive part. FIG. 2 shows these further constituents which are required for filling the capsules 2, 3 or 2', 3 and for changing the various media to be used successively (for example aldehyde solution for the first fixation, buffer without aldehyde, $OsO_4$ solution for the second fixation, buffer without $OsO_4$, dehydration stages with 50%, 75%, 90% and 100% acetone, 3:1, 1:1 and 1:3 acetone/monomer mixtures, pure monomer in the standard method for synthetic resin embedding or substitution medium, washing fluid, mixing stages between washing fluid and monomer batch, pure monomer batch in the cryosubstitution method or buffered aldehyde solution for fixation, buffer as washing fluid, methanol/water mixtures with 50%, 75% and 90% methanol, pure anhydrous methanol changed three times, 3:1, 1:1 and 1:3 mixtures between methanol and monomer batch, pure monomer batch in the PLT method).

FIGS. 2a and b show a container 10 for filling and taking up the hole capsules 2 or 2', which contain, at the mutual axial distance D, at least two bores 11 having a diameter (A+T) for inserting the hole capsules 2 or 2'. The diameter of these bores 11 exceeds the diameter A of the hole capsules 2 or 2' by the amount of tolerance T (about 0.5 to 1 mm) which, under all known experimental conditions, ensures easy insertion and easy removal of the hole capsules 2 or 2'. The bores can be of stepped design for the insertion of hole capsules 2' with the beaded edge 27. Between the two bores 11, there is a larger orifice 24 for taking up a substitution body 12 which can have a coaxial central bore 13 and an attachment (for example a further bore 14) for taking up a manipulator (for example a cryomanipulator 9 with a thread) and a rotation preventer (for example a bolt 15) and can be moved up and down in the orifice 24. The diameter of the orifice 24 and that of the substitution body 12 as well as the bottom of the substitution body 12 are designed such that the media, which are filled into the preferably centrally arranged channel 13 and are to be withdrawn through the latter, can rapidly move through a gap S'. Finally, in a further embodiment of the invention, the container 10 can be provided with a draw-up rim 16 which prevents an overflow of media during the up-and-down movement of the substitution body 12.

As a further constituent of the system according to the invention or for carrying out the method according to the invention, FIG. 2c shows a container 17 for filling and taking up the enveloping capsules 3 by the carrier 1, 4 or 1, 4' which, in its general arrangement, largely corresponds to the container 10. Again, it has at least two bores 18 for taking up the enveloping capsules 3, whose parallel axes are located correspondingly to the axes of the two rams 4 and 4' on the carrier 1, for example at a mutual distance D. In view of the greater external diameter B of the enveloping capsules, the diameter of the bores 18 is in this case (B+T), T again having to be understood as an amount of tolerance in the sense already explained. Between the two bores 18, there is again a central bore 26 whose volume at least corresponds to the volume of all the bores 18 for taking up the enveloping capsules 3. Analogously to the container 10, the rim 19 of the container 17 is drawn up as a protection against lateral flowing-off of the excess monomer batch, when the hole capsules 2 or 2' are immersed for slipping on the enveloping capsules 3.

For the purpose of carrying out, according to the method, the low-temperature polymerization by means of UV irradition, the arrangement according to the invention has moreover, according to FIG. 2d, a pot 20 with a central stand 21, onto which the carrier 1, 4 or 1, 4' charged with the capsules 2, 3 or 2', 3 can be placed or slipped over it. The inner walls of the pot 20 reflect the UV entering from above from a UV emitter, in such a way that the UV action takes place in the capsule system 2, 3 or 2', 3 above all from below and therefore first polymerizes the polymer 5 in the region of the objects 7. This is important for methodical reasons (cf. the cited literature). For removing the heat which is generated during the exothermic polymerization reaction, the pot 20 is filled with a fluid 22 (for example alcohol) approximately up to the lower boundary of the rams 4, but at most up to the upper rim of the enveloping capsules 3.

Carrying out the method according to the invention by means of the system according to the invention is extremely simple. In the simplest case, a hole capsule 2 or 2' loaded with a slide 7 is immersed onto the ram 4 or 4' into the first medium (for example aldehyde solution or substitution medium 31 in the container 30) by means of tweezers or a simple manipulator which essentially consists off a sleeve 9' with a handle 29. For generating convection or degrading of gradients on the object surface, brief lifting and relowering of the capsule 2 or 2' suffices. When the incubation is complete, the capsule 2 or 2' is lifted and, after the medium has run out, transferred into the next medium. When the incubation in the monomer batch 5 is complete, the hole capsule 2 or 2' is provided according to FIG. 1 with an enveloping capsule 3 and passed to the thermal polymerization or UV polymerization.

According to an embodiment of the invention, the empty hole capsules 2 or 2' are inserted into the orifices 11 of a container 10 and together with the latter, in the case of a cryopreparation, cools to the desired temperature (for example −80° C.) in a cooling system. After insertion of the objects 7, which may have been frozen, the quantity of liquid medium present in or filled into a central orifice 24 of the container 10 for filling the hole capsules 2 or 2' is slowly lifted by the substitution body 12 which has also been precooled if necessary: the capsules 2 or 2' are then filled through the bore 6 with the cold medium which can be extracted again through the central channel 13 of the substitution body and replaced by a new medium. During the incubation, synchronous movement of the fluid in the capsules 2 or 2' is possible by simple lifting or lowering of the substitution body 12. After repeated change of media, pure monomer batch 5 is present in all the capsules. All the capsules 2 or 2' are then slipped over the rams 4 or 4' located on the carrier 1 and transferred thereon. Beforehand, the enveloping capsules 3 in the orifices 18 of the container 17 are likewise filled with cold monomer 5, and the filled hole capsules 2 or 2' are then inserted with the carrier 1, 4 or 1, 4' into the enveloping capsules 3 for sealing the orifices 6. The enveloping capsules 3 adhere in strict sliding fit either to the second step of the stepped ram 4 or to the beaded edge 27 of the hole capsule 2' which in turn is located in strict sliding fit on a ram 4'. The excess monomer flows out of the enveloping capsules 3 into the central orifice 26 of the container 17. The loaded carrier 1, 4, 2, 3 or 1, 4', 2', 3 is then transferred by the manipulator 9 to the stand 21 in the pot 20, and the UV polymerization is carried out in the manner already described, according to FIG. 2d. For a subsequent thermal polymerization, this system is transferred by the manipulator 9 into a thermostat.

The method according to the invention can be accomplished in various modifications and combinations of the arrangement explained by way of example by reference to FIGS. 1 and 2, without thereby losing its inventive character. Thus, instead of two twin capsules 2, 3 or 2', 3, substantially more capsules can and will be charged in practice in one working step, as indicated by way of example in FIG. 2a by the orifices 11' shown in broken lines. The geometrical form and arrangement of the capsules on the carrier 1 or in the containers 10 and 17 is irrelevant. The materials (for example PE, PP, acetal resin, gelatine or aluminum, stainless steel) from which, and the methods (for example replication, injection-moulding) by which, the capsules and/or the containers and other parts of the arrangement are made are also irrelevant. Finally, an essential advantage of the twin capsule arrangement according to the invention in terms of the method is that this principle or system can be used with any technically known method or system for the automatic processing of biological specimens for subsequent preparation of sections or histochemical and biochemical investigation, only the first step (charging of the hole capsules 2 or 2' with specimens 7) having to be carried out manually, but in all other steps an automatic sequence without intervention of the user and hence also without the risk of skin contact with allergens or inhalation of gaseous toxic substances can be carried out even without spending extra time.

We claim:

1. A method for embedding a specimen comprising placing a specimen into a hole capsule comprising a container that is open at the top and in the lower third of the container has at least one passage orifice which is smaller than the diameter of the specimen, filling via the at least one passage orifice the hole capsule with one or more of a dehydration or substitution media, then removing the media through the at least one passage orifice, and then filling via the at least one passage orifice the hole capsule with a polymerizable fluid, introducing the hole capsule containing the specimen into an enveloping capsule that contains said polymerizable fluid, such that the polymerizable fluid fills a gap between the hole capsule and the enveloping capsule, wherein the enveloping capsule together with the hole capsule arranged therein and the specimen in the hole capsule, and the polymerizable fluid in the hole capsule and in the enveloping capsule, are lifted and introduced into a polymerization vessel, and embedding the specimen in the hole capsule by polymerization of the polymerizable fluid under the action of UV light, wherein the hole capsule and enveloping capsule are joined together by a holder.

2. A method according to claim 1, wherein the hole capsule and the enveloping capsule each have a cylindrical wall.

3. A method according to claim 1, wherein the specimen is frozen and the placing, filling, introducing, and embedding steps are carried out below 0° C.

4. A method according to claim 1, wherein the polymerizable fluid is organic.

5. A method according to claim 1, wherein the enveloping capsule is UV-permeable, and the UV light strikes the enveloping capsule and hole capsule from below.

6. A method according to claim 1, wherein the polymerizable fluid introduced into the hole capsule is a polymerizable monomer, which is polymerized during the embedding step.

7. A method according to claim 1, wherein the polymerization is carried out at a temperature between −120° C. and +80° C., and which further comprises after the embedding step, preparation of one or more sections of the specimen for microscopic or histochemical investigations.

8. A method according to claim 1, wherein a plurality of specimens are placed into a plurality of hole capsules, and the plurality of hole capsules are introduced into a plurality of enveloping capsules.

9. A method according to claims 1, wherein the at least one passage orifice comprises a plurality of orifices that each have a diameter that permits the ingress and egress of fluids but precludes egress of the specimen.

10. A method according to claim 1, wherein the filling of the media into the hole capsule comprises immersing the hole capsule into the media, thereby allowing the media to flow through the at least one orifice into the hole capsule.

11. A method according to claim 1, wherein the hole capsule and enveloping capsule are joined together by said holder, and wherein during the polymerization, the holder closes the tops of the hole capsule and enveloping capsule to provide an airtight system.

12. A method according to claim 1, wherein the gap is about 0.5 to 2 mm.

13. A method according to claim 1, wherein the filling comprises lowering the hole capsule into the media whereby the media flows through the at least one passage orifice into the hole capsule, lifting the hole capsule out of the media such that the media flows out of the hole capsule through the at least one passage orifice, and then lowering the hole capsule into the polymerizable fluid that comprises a liquid monomer.

14. A method according to claim 1, wherein so as to provide improved heat removal, the UV irradiation takes place while the enveloping capsule is immersed in a fluid bath in as the vessel.

15. A method according to claim 14, wherein the fluid bath is an alcohol bath.

16. A method according to claim 1, wherein a plurality of hole capsules are filled at the same time with the media, wherein the plurality of hole capsules are transferred together by means of said holder, which engages simultaneously all the hole capsules, into a plurality of enveloping capsules.

17. A method according to claim 16, wherein the plurality of hole capsules are transferred together with the plurality of enveloping capsules at the same time to the embedding step.

18. A method according to claim 16, wherein the holder holds the hole capsules at the tops of the hole capsules.

* * * * *